United States Patent
Nagale et al.

(10) Patent No.: US 9,492,113 B2
(45) Date of Patent: Nov. 15, 2016

(54) SYSTEMS AND METHODS FOR MONITORING ORGAN ACTIVITY

(75) Inventors: Sandra Nagale, Lowell, MA (US); Ruth Cheng, Natick, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 41 days.

(21) Appl. No.: 13/535,741

(22) Filed: Jun. 28, 2012

(65) Prior Publication Data

US 2013/0018281 A1  Jan. 17, 2013

Related U.S. Application Data (60) Provisional application No. 61/508,169, filed on Jul. 15, 2011.

(51) Int. Cl.
*A61B 5/103* (2006.01)
*A61B 5/117* (2016.01)
(Continued)

(52) U.S. Cl.
CPC .......... *A61B 5/205* (2013.01); *A61B 5/036* (2013.01); *A61B 5/103* (2013.01); *A61B 5/107* (2013.01); *A61B 5/1076* (2013.01); *A61B 5/202* (2013.01); *A61B 5/204* (2013.01); *A61B 5/42* (2013.01); *A61B 5/4839* (2013.01); *A61B 5/4848* (2013.01); *A61B 5/6859* (2013.01); *A61B 5/6874* (2013.01);
(Continued)

(58) Field of Classification Search
CPC .......... A61B 5/036; A61B 5/42; A61B 5/103; A61B 5/107; A61B 5/1076; A61B 5/202; A61B 5/204; A61B 5/205; A61B 5/207; A61B 5/208; A61B 5/6874; A61B 5/6885; A61B 5/6859; A61B 2018/0016; A61B 2019/464; A61B 2019/465; A61B 2562/04; A61B 2562/046
See application file for complete search history.

(56) References Cited

U.S. PATENT DOCUMENTS 5,127,077 A  6/1992 Iyer et al.
5,156,151 A  10/1992 Imran
(Continued)

FOREIGN PATENT DOCUMENTS

WO  WO 2005/067791  7/2005
WO  WO 2012/083155 A2  6/2012

OTHER PUBLICATIONS

Gulur, et al., "Management of Overactive Bladder," Nature Reviews/Urology, Oct. 2010, vol. 7, pp. 572-582.
(Continued)

*Primary Examiner* — Devin Henson
(74) *Attorney, Agent, or Firm* — Bookoff McAndrews, PLLC (57) ABSTRACT

A medical device for monitoring physical, chemical, or biological characteristics of an organ, such as the urinary bladder. The medical device may include an elongate member having a proximal end and a distal end. The device may further include an end-effector assembly extending distally from the distal end of the elongate member. The end-effector assembly may also include a plurality of sensing elements for detecting abnormal organ function. Each of the plurality of sensing elements may include one or more of mechanical, visual, chemical, and biological sensors.

20 Claims, 6 Drawing Sheets

(51) Int. Cl.
*A61B 5/20* (2006.01)
*A61B 5/00* (2006.01)
*A61B 5/03* (2006.01)
*A61B 5/107* (2006.01)

(52) U.S. Cl.
CPC .......... *A61B 5/6885* (2013.01); *A61B 2562/04* (2013.01); *A61B 2562/046* (2013.01)

(56) References Cited

U.S. PATENT DOCUMENTS

| | | | |
|---|---|---|---|
| 5,261,889 A | 11/1993 | Laine et al. | |
| 5,277,201 A | 1/1994 | Stern | |
| 5,293,869 A | 3/1994 | Edwards et al. | |
| 5,309,910 A | 5/1994 | Edwards et al. | |
| 5,313,943 A | 5/1994 | Houser et al. | |
| 5,324,284 A | 6/1994 | Imran | |
| 5,345,936 A * | 9/1994 | Pomeranz | A61B 5/0422 600/374 |
| 5,348,554 A | 9/1994 | Imran et al. | |
| 5,366,490 A | 11/1994 | Edwards et al. | |
| 5,370,675 A | 12/1994 | Edwards et al. | |
| 5,435,805 A | 7/1995 | Edwards et al. | |
| 5,471,982 A | 12/1995 | Edwards et al. | |
| 5,486,161 A | 1/1996 | Lax et al. | |
| 5,545,171 A | 8/1996 | Sharkey et al. | |
| 5,545,193 A | 8/1996 | Fleischman et al. | |
| 5,588,960 A | 12/1996 | Edwards et al. | |
| 5,617,876 A | 4/1997 | van Duyl | |
| 5,636,634 A | 6/1997 | Kordis et al. | |
| 5,662,108 A | 9/1997 | Budd et al. | |
| 5,704,353 A * | 1/1998 | Kalb et al. | 600/342 |
| 5,706,809 A | 1/1998 | Littmann et al. | |
| RE35,880 E | 8/1998 | Waldman et al. | |
| 5,836,874 A | 11/1998 | Swanson et al. | |
| 5,849,011 A | 12/1998 | Jones et al. | |
| 5,860,974 A | 1/1999 | Abele | |
| 5,893,885 A | 4/1999 | Webster, Jr. | |
| 5,961,513 A | 10/1999 | Swanson et al. | |
| 5,964,796 A | 10/1999 | Imran | |
| 6,006,755 A | 12/1999 | Edwards | |
| 6,009,877 A | 1/2000 | Edwards | |
| 6,014,579 A | 1/2000 | Pomeranz et al. | |
| 6,038,472 A | 3/2000 | Williams et al. | |
| 6,056,744 A | 5/2000 | Edwards | |
| 6,073,052 A | 6/2000 | Zelickson et al. | |
| 6,088,610 A | 7/2000 | Littmann et al. | |
| 6,115,626 A | 9/2000 | Whayne et al. | |
| 6,156,029 A | 12/2000 | Mueller | |
| 6,296,608 B1 | 10/2001 | Daniels et al. | |
| 6,416,505 B1 * | 7/2002 | Fleischman | A61B 18/1482 606/1 |
| 6,463,331 B1 | 10/2002 | Edwards | |
| 6,571,127 B1 | 5/2003 | Ben-Haim et al. | |
| 6,645,201 B1 | 11/2003 | Utley et al. | |
| 6,660,003 B1 | 12/2003 | DeVore et al. | |
| 6,673,070 B2 | 1/2004 | Edwards et al. | |
| 6,692,490 B1 * | 2/2004 | Edwards | 606/41 |
| 6,994,704 B2 | 2/2006 | Qin et al. | |
| 7,022,105 B1 | 4/2006 | Edwards | |
| 7,056,320 B2 | 6/2006 | Utley et al. | |
| 7,125,407 B2 | 10/2006 | Edwards et al. | |
| 7,165,551 B2 * | 1/2007 | Edwards | A61B 5/04884 128/898 |
| 7,326,235 B2 | 2/2008 | Edwards | |
| 7,615,014 B2 * | 11/2009 | Omata et al. | 600/587 |
| 7,648,500 B2 | 1/2010 | Edwards et al. | |
| 7,742,795 B2 | 6/2010 | Stone et al. | |
| 7,850,685 B2 | 12/2010 | Kunis et al. | |
| 8,177,781 B2 | 5/2012 | Thomas et al. | |
| 8,672,923 B2 | 3/2014 | Ladtkow et al. | |
| 2001/0009976 A1 | 7/2001 | Panescu et al. | |
| 2002/0013581 A1 | 1/2002 | Edwards et al. | |
| 2002/0026188 A1 | 2/2002 | Balbierz et al. | |
| 2002/0072742 A1 | 6/2002 | Schaefer et al. | |
| 2003/0055307 A1 | 3/2003 | Elmaleh et al. | |
| 2003/0212394 A1 | 11/2003 | Pearson et al. | |
| 2004/0068203 A1 * | 4/2004 | Gellman | A61B 5/22 600/587 |
| 2004/0153058 A1 | 8/2004 | West et al. | |
| 2004/0176755 A1 | 9/2004 | Lafontaine | |
| 2006/0173359 A1 | 8/2006 | Lin et al. | |
| 2007/0282184 A1 * | 12/2007 | Roberts | 600/345 |
| 2008/0009747 A1 | 1/2008 | Saadat et al. | |
| 2008/0015569 A1 | 1/2008 | Saadat et al. | |
| 2008/0215040 A1 | 9/2008 | Paithankar et al. | |
| 2010/0166739 A1 | 7/2010 | Chancellor et al. | |
| 2012/0265198 A1 * | 10/2012 | Crow et al. | 606/41 |
| 2013/0035576 A1 | 2/2013 | O'Grady et al. | |
| 2013/0090640 A1 | 4/2013 | Nagale et al. | |
| 2013/0090648 A1 | 4/2013 | Nagale et al. | |

OTHER PUBLICATIONS

Gillespie, et al., "On the Origins of the Sensory Output from the Bladder: the Concept of Afferent Noise," *BJU International*, 2009, vol. 103, pp. 1324-1333.

Steers, William D., "Pathophysiology of Overactive Bladder and Urge Urinary Incontinence," *Reviews in Urology*, 2002, vol. 4, Suppl 4, pp. S7-S18.

Charlton et al., "Focal changes in nerve, muscle and connective tissue in normal and unstable human bladder," *BJU International*, 1999, pp. 953-960, 84.

Drake et al., Model of peripheral autonomous modules and a myovesical plexus in normal and overactive bladder function, *The Lancet*, 2001, pp. 401-403, 358.

Mustafa et al., "Cooling-induced bladder contraction: studies on isolated detrusor muscle preparations in the rat," *Urology*, 1999, pp. 653-657, 53.

Roosen et al., "Characteristics of spontaneous activity in the bladder trigone," *European Urology*, 2009, pp. 346-354, 56.

Lemke et al., "Multisensor array for pH, $K^+$, $Na^+$ and $Ca^{2+}$ measurements based on coated-film electrodes," *Sensors and Actuators B*, 1992, pp. 488-491, 7.

Kuo et al., "Novel Biomarkers for Diagnosis and Therapeutic Assessment of Overactive Bladder: Urinary Nerve Growth Factor and Detrusor Wall Thickness," *LUTS*, 2009, pp. 559-561, 1.

T. Hague et al., "The effect of heating (37-41 degrees C)on detrusor contractile function in rabbit mucosa-intact and denuded preparations," Neurology and Urodynamics, Beijing, People R. China: $42^{nd}$ Annual Meeting of International Continence Society (ICS) vol. 31 (6), pp. 1027-1028.

T. Hague et al., "ICS 2012 Abstract Form, $42^{nd}$ Annual Meeting of the International Continence Society, Oct. 15-19, 2012, Beijing China," 2 pages.

Partial International Search Report issued in PCT/US2012/059028, mailed Jan. 23, 2013, 2 pages.

* cited by examiner

SYSTEMS AND METHODS FOR MONITORING ORGAN ACTIVITY

CROSS-REFERENCE TO RELATED APPLICATIONS

This patent application claims the benefits of priority under 35 U.S.C. §§119-120 to U.S. Provisional Application No. 61/508,169, filed on Jul. 15, 2011, the entirety of which is incorporated herein by reference.

FIELD OF THE INVENTION

This disclosure relates generally to systems and methods for detecting urinary tract conditions and the effects of therapy thereon. More particularly, embodiments of the claimed invention relate to sensing elements for detecting conditions symptomatic of conditions such as bladder overactivity.

BACKGROUND OF THE INVENTION

Often patients and physicians discover ailments or diseases too late, making it difficult to treat a patient in time to effect timely therapy. Monitoring body organs regularly and effectively, therefore, can make the difference between saving and losing a life. Even for diseases that have positive prognosis, monitoring the disease over its lifetime can help administer appropriate therapy, including, but not limited to, drugs, electrical stimulation, or other known therapies, at suitable times, study different stages of the disease, and improve the patient's condition.

For example, the etiology of an overactive bladder (OAB) syndrome, which affects approximately 50 million patients worldwide, is still not well understood, and the commonly prescribed non-invasive primary treatment (e.g., drugs) is ineffective for approximately 40% of those patients. For patients that do not react well to drugs, other treatments (such as neural stimulation), or surgery are significantly more effective. But these treatments are not readily prescribed due to the high invasiveness and other adverse effects related with these procedures.

Physicians usually monitor drug effectiveness by conducting urodynamics (a study that assesses how the bladder and urethra perform their job of storing and releasing urine) and monitoring urine urgency and frequency. They are, however, unable to quickly assess whether a drug favorably affects the bladder, and to what extent. For example, it is difficult to discern whether a drug has affected urothelium sensitization, detrusor over-activity, nerve firing, and other such events.

If, over time, favorable results are not observed, patients are typically advised to change the current drug treatments. Because discovering an effective drug treatment takes time, the disease may progress significantly during this period. Further, if drug treatments are ineffective, selective screening may be required before patients undergo more invasive treatments such as neural stimulation.

In addition to these problems, shedding light on the effectiveness of a drug or other OAB therapies earlier in the treatment course enables selection of the most effective treatment without unnecessary delays. As the OAB disease stage varies significantly among patients, monitoring a disease's progression (by monitoring changes in bladder wall pathology and morphology, or presence of indicative biomarkers in urine, for example) may be critical. With such information at hand, the physician can appropriately treat a patient earlier in the course of disease progression.

Presently, physicians are unable to closely monitor patients' progress or their disease stage. In addition, physicians are unable to readily determine the efficacy of certain treatments, such as drug therapies on the patient. In light of these issues, there exists a need for an improved monitoring system that allows physicians to monitor organ activity in real time or near real time.

SUMMARY OF THE INVENTION

Embodiments of the present disclosure are directed to systems and methods for monitoring physical, chemical, or biological characteristics of an organ, such as the urinary bladder.

One embodiment of the present disclosure is directed to a medical device. The medical device may include an elongate member having a proximal end and a distal end. The device may further include an end-effector assembly extending distally from the distal end of the elongate member. The end-effector assembly may include a plurality of sensing elements for detecting abnormal organ function, wherein the plurality of sensing elements includes one or more of mechanical, chemical, and biological sensors.

In various embodiments, the medical device may include one or more of the following additional features: the end-effector assembly may include a plurality of steerable legs; the end-effector assembly may include a plurality of legs extending from a proximal end of the end-effector assembly to a distal end of the end-effector assembly, the plurality of legs forming a three-dimensional shape; the three-dimensional shape may be configured to transition between a compressed delivery configuration and an expanded deployed configuration; the end-effector assembly may include an inflatable member and the sensing elements may be disposed on an exterior surface of the inflatable member; the plurality of sensing elements may be configured to detect changes in one of a urinary structure and a urine within a bladder; the plurality of sensing elements may be configured to wirelessly transmit sensed data to an external component; and the plurality of sensing elements may include at least one of a pressure sensor, a flow sensor, a displacement sensor, a vibration sensor, a voltage sensor, a Doppler sensor, a chemical sensor, or a biosensor.

Another embodiment of the present disclosure may be directed to a medical system for monitoring a urinary system of a patient. The medical device may include a wireless sensor configured to detect changes in one of a bladder and urine of a patient. The changes detected by the medical device may include one of mechanical, chemical, or biological changes, and the wireless sensor may be configured for extended implantation within the patient. The medical device may further include an external component configured to receive data from the wireless sensor.

In various embodiments, the medical device may include one or more of the following additional features: the wireless sensor may include at least one of a pressure sensor, a flow sensor, a displacement sensor, a vibration sensor, a voltage sensor, a Doppler sensor, a chemical sensor, or a biosensor; the wireless sensor may be biodegradable; the wireless sensor may include an anchoring element for securing the wireless sensor to a bladder wall; the wireless sensor may include a first portion configured to be secured to an internal surface of a bladder wall and a second portion configured to be secured to an external surface of a bladder wall; the first and second portions may be configured to measure a thickness of the bladder wall; the wireless sensor may include a band sensor configured to surround a portion of the bladder; a urea sensor configured to detect bladder filling; the wireless sensor may be disposed within a mechanical casing capable of shielding the wireless sensor; and the wireless sensor may be coupled to a medical device configured to deliver therapy to the urinary system.

A further aspect of the present disclosure describes a method for monitoring a urinary bladder. The method may include the step of inserting a medical device within a vesicle of a urinary tract. The inserted medical device may include an elongate member having a proximal end and a distal end and an end-effector assembly extending distally from the distal end of the elongate member. The end-effector assembly may include a plurality of sensing elements for detecting abnormal organ function, wherein the sensing elements may include one or more of mechanical, chemical, and biological sensors. The method may further include the steps of positioning the medical device adjacent a wall of the bladder, and measuring at least one of a physical, chemical, or biological property of the bladder.

In various embodiments, the method may further include one or more of the following additional features: the end-effector assembly may include a plurality of steerable legs; and the plurality of sensing elements may include at least one of a pressure sensor, a flow sensor, a displacement sensor, a vibration sensor, a voltage sensor, a Doppler sensor, a chemical sensor, or a biosensor.

Additional objects and advantages of the present disclosure will be set forth in part in the description which follows, and in part will be obvious from the description, or may be learned by practice of the present disclosure. The objects and advantages of the present disclosure will be realized and attained by means of the elements and combinations particularly pointed out in the appended claims.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate exemplary embodiments of the present disclosure and together with the description, serve to explain the principles of the disclosure.

DESCRIPTION OF THE EMBODIMENTS

Reference will now be made in detail to embodiments of the present disclosure, an example of which is illustrated in the accompanying drawings. Wherever possible, the same reference numbers will be used throughout the drawings to refer to the same or like parts.

Overview

Embodiments of the present disclosure relate to systems and methods for monitoring abnormal organ activity. To this end, some embodiments introduce a sensing element that may be positioned inside, outside, or around an organ, or implanted in organ walls to measure characteristics such as physical, mechanical, or biochemical changes associated with certain diseases. The various sensing element embodiments described here may be used to measure the characteristics of any body organ, such as the stomach, bladder, intestines, bowel, or urinary tract, without departing from the scope of the present disclosure. Moreover, the sensing elements may be inserted during medical procedures or they may be implanted to continuously monitor the organ for an extended length of time. Implantable sensing elements may be fabricated from biodegradable material that simply degrades or metabolizes over time or is flushed out during normal bodily functions.

In the following sections, embodiments of the present disclosure will be described using an exemplary body organ—the urinary bladder. It will be understood that this choice is merely exemplary and that the device may be utilized in any other organ. In the urinary bladder, the sensing element may measure physical, mechanical, or biochemical changes associated with bladder diseases such as overactive bladder, bladder sphincter dyssynergia, or arrhythmia.

Exemplary Embodiments

Figure 1:
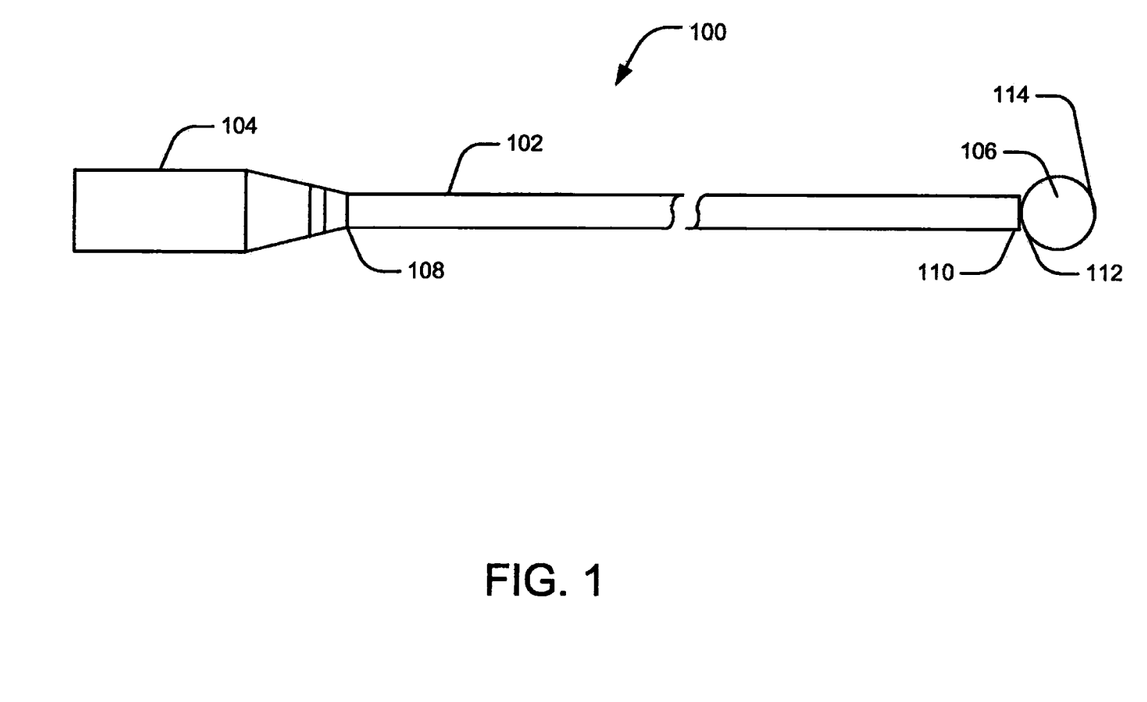
FIG. 1 illustrates a medical device for monitoring organ activity according to an embodiment of the present disclosure.

FIG. 1 illustrates an exemplary medical device 100, which includes an elongate member 102, a handle portion 104, and an end-effector assembly 106. Elongate member 102 may have a proximal end 108 and a distal end 110. Further, end-effector assembly 106 may likewise have a proximal end 112 and a distal end 114. For purposes of this disclosure, "proximal" refers to the end closer to the device operator during use, and "distal" refers to the end further from the device operator during use. Handle portion 104 is disposed at the elongate member's proximal end 108, while end-effector assembly 106 is disposed at its distal end 110.

Elongate member 102 extends from the handle portion 104 to the end-effector assembly 106. This member may be a rod or tube, suitable for advancing the end-effector assembly 106 into an operating position. Alternatively, elongate member 102 may have any cross-sectional shape or configuration that can be received in the lower urinary tract. In one embodiment, elongate member 102 has a substantially circular cross-section, similar to the generally circular cross-section body cavities and lumens.

The elongate member 102 may be made from any suitable material having sufficient flexibility to traverse body cavities and tracts. Such materials may include, but are not limited to, synthetic plastics, polymers, stainless steel, and metals, including polymers and alloys, and other materials known to the art. In one embodiment, the material forming elongate member 102 may be a shape memory alloy such as nitinol, a nickel-titanium alloy.

Figure 2:
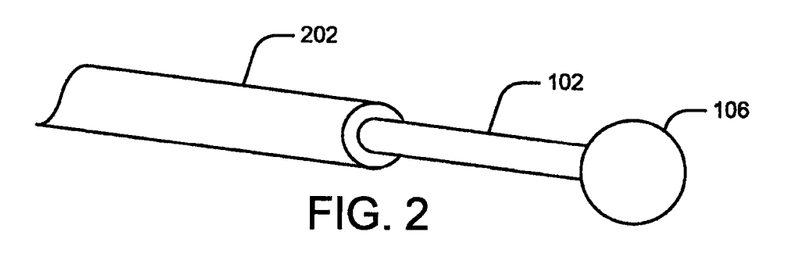
FIG. 2 illustrates the medical device of FIG. 1 enclosed in a sheath according to one embodiment of the present disclosure.

As seen in FIG. 2, an embodiment of medical device 100 includes an outer sheath 202, which may surround elongate member 102 and end-effector assembly 106, from the elongate member's proximal end 108 to the end-effector assembly's distal end 114. Sheath 202 preferably has the same cross-sectional shape as elongate member 102 and fully covers elongate member 102 or end-effector assembly 106. When end-effector assembly 106 is within outer sheath 202, the medical device 100 may be inserted into a body cavity or surgically advanced to the desired site. When medical device 100 is positioned at the desired location, sheath 202 may be pulled proximally or elongate member 102 may be pushed distally so that end-effector assembly 106 extends out of the sheath's distal end into an operating state.

In some embodiments, the diameter of end-effector assembly 106 in the operating state may be greater than the diameter of outer sheath 202. In these situations, end-effector assembly 106 may be inserted into outer sheath 202 in a collapsed or folded state. To this end, end-effector assembly 106 may be made of self-expandable materials, such as memory alloys (Nitinol). Alternatively, end-effector assembly 106 may include a balloon. When the end-effector assembly 106 is actuated, the balloon may be inflated, which in turn may expand end-effector assembly 106 into an operating state. As discussed in greater detail below, when expanded, end-effector assembly 106 may be configured to conform to the shape of a bladder and/or distend bladder walls to sufficiently position the disclosed sensors against the bladder wall. It will be understood that any other method may be utilized to expand end-effector assembly 106 without departing from the scope of the present invention.

The end-effector assembly's actuation described here may be carried out by any actuation mechanism known now or that may be known in the future without departing from the scope of the present disclosure. For example, a pulling or pushing mechanism may be incorporated in handle portion 104 allowing the physician to easily deploy end-effector assembly 106 when required. For purposes of this disclosure, sheath 202 may include one or more lumens to insert various devices into the body cavities. For example, the sheath may include two lumens, one for passing a sensing element, while the second lumen may be utilized to pass an irrigation or suction device. Moreover, the sheath may be formed of materials such as polyamide, polyurethane, rubber, or any other suitable material.

Various aspects of the end-effector assembly 106 are shown in FIGS. 3-6. As shown in FIGS. 3A and 3B, the end-effector assembly 106 can include single (FIG. 3A) or multiple (FIG. 3B) sensing elements 302, which extend distally from elongate member 102 to monitor a body organ, such as the bladder and/or other associated structures of the urinary system, including, but not limited to, the bladder neck and surrounding nerves and/or vasculature. As shown, a leg 304 may connect the elongate member 102 and sensing elements 302. Moreover, various types of sensing elements (mechanical, chemical, or biological) may be incorporated in the same medical device 100 without departing from the scope of the present disclosure. In some embodiments, sensing elements 302 may include an imaging device or system. In such embodiments, the imaging devices may include any suitable technique, including, e.g., direct visualization with a camera, ultrasound, magnetic resonance imaging, infrared, computed tomography, and x-ray. Sensing elements 302 may be wireless devices attached to the distal end of elongate member 102 or they may be wired devices. For wired devices, elongate member 102 may include one or more lumens 402 (illustrated in FIG. 4), extending from the elongate member's proximal end 108 to its distal end 110. Electrical and data connections or cables may extend through these lumens 402 to the proximal end 108 of handle portion 104.

Figure 3A:
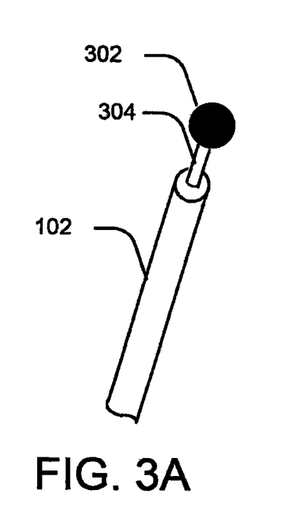
FIG. 3A illustrates an exemplary embodiment of an end-effector assembly of FIG. 1.
Figure 3B:
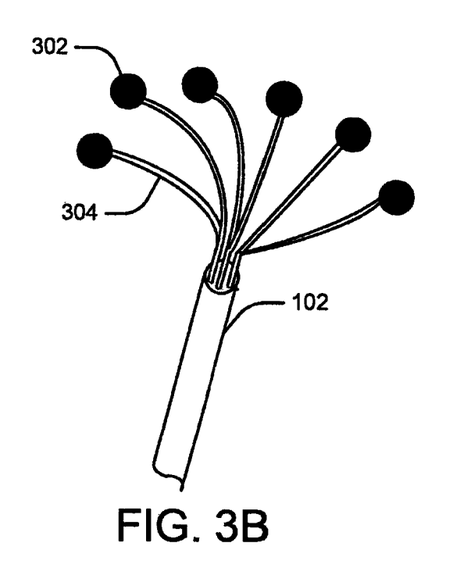
FIG. 3B illustrates another exemplary embodiment of the end-effector assembly of FIG. 1.
Figure 4:
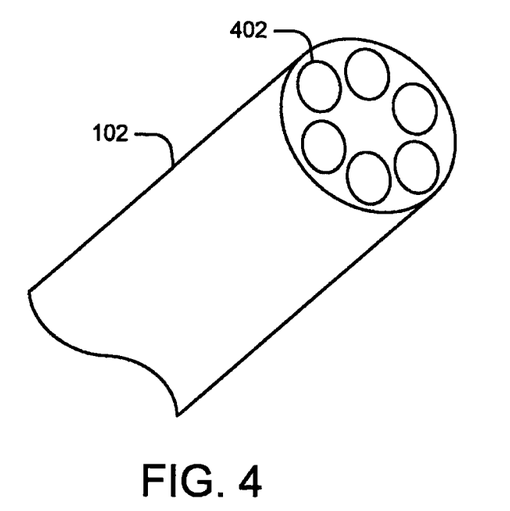
FIG. 4 illustrates an exemplary elongate member with multiple lumens according to an embodiment of the present disclosure.

Although FIG. 3B illustrates only six such lumens 402 within the elongate member 102, those of ordinary skill will understand that elongate member 102 may include a greater or lesser number of lumens. These lumens 402 may receive cables or other electrical connections from sensing elements 302. In one embodiment, one lumen 402 may receive connections for one sensing element 302. Alternatively, a single lumen 402 may house multiple cables and connections stemming from multiple sensing elements 302. It is to be understood that lumens 402 may have any size, cross-sectional area, shape, or configuration. It will further be understood that the number of lumens and their arrangement may depend on the number of sensing elements on end-effector assembly 106 and the required application.

Figure 5:
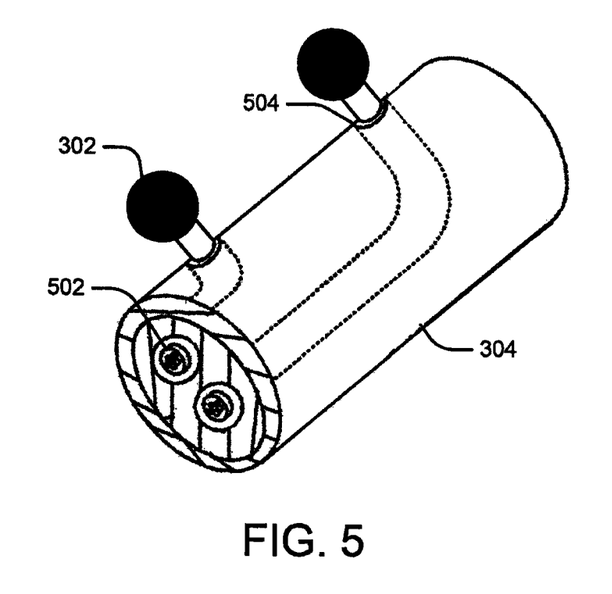
FIG. 5 is an exploded view of a portion of a leg of an end-effector assembly according to embodiments of the present disclosure.

In some versions, as illustrated in FIG. 5, end-effector assembly 106 may include one or more legs 304 connecting elongate member 102 and sensing elements 302. Alternatively, end-effector assembly 106 may include multiple legs 304, each with one or more sensing elements 302. Leg 304 may be selectively steerable or stationary depending on the application. Moreover, in case of multiple legs, legs 304 may be individually steered or steered together. The steering mechanism for end-effector assembly 106 may be disposed close to the elongate member's proximal end 108 or in handle portion 104. It will be understood that various steering mechanisms exist and any one of these mechanisms may be utilized to steer the sensing elements 302. For example, the mechanism may be mechanical, electronic, or electro-mechanical. Once end-effector assembly 106 is inserted in the bladder and/or positioned proximate associated urinary structure, for example, end-effector assembly 106 may be actuated to extend out of sheath 202 and each individual sensing element 302 may be steered to its desired location.

Further, leg 304 may be a solid rod or a tube. Tubular legs may include one or more lumens 502 (illustrated in FIG. 5) extending longitudinally. Lumens 502 may be in communication with a corresponding lumen 402 of elongate member 102 and may extend from proximal end 112 of end-effector assembly 106 to an exit aperture 504 on leg 304. Data or electrical connections, or cables such as optical fibers may be disposed within lumen 502 to power sensing elements 302, receive measured signals, or measure certain characteristics. Moreover, in some embodiments, an optical fiber may also be present within lumen 502. Wire connections may terminate at each sensing element 302 within a lumen 502 or a single wire connection may include connections to multiple sensing elements 302 on a leg without departing from the scope of the present disclosure.

Figure 6A:
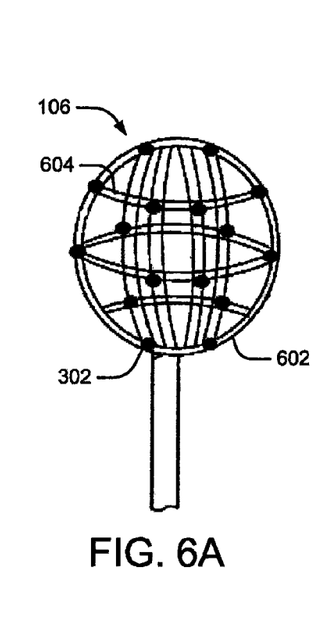
FIGS. 6A-E illustrates alternative configurations of exemplary medical devices for monitoring organ activity according to some embodiments of the present disclosure.

End-effector assembly 106 may assume any shape or configuration that can be received in the lower urinary tract. For example, end-effector assembly 106 may include an array of sensor elements distributed in any suitable fashion. FIGS. 6A-6E illustrates some alternative end-effector assembly 106 configurations according to embodiments of the present disclosure. It will be understood that these figures illustrate end-effector assemblies including inflatable members with sensing elements 302 disposed on the exterior surface of the members. The figures illustrate these end-effector assemblies in their inflated or operating state. Within sheath 202, these assemblies may be in a folded or collapsed state. FIG. 6A illustrates an end-effector assembly 106 including multiple longitudinal members, such as legs 602 extending from proximal end 112 to distal end 114 of end-effector assembly 106 forming an inflatable three-dimensional shape, such as a sphere, in the operable state. In some embodiments, end-effector assembly 106 may also include one or more circumferentially extending members, such as circumferential legs 604. Here, the legs may include one or more sensing elements 302 disposed at exterior exit apertures 504 in the legs. When end-effector assembly 106 is inserted into the urinary bladder and inflated, legs 602 may be disposed adjacent to the bladder walls, allowing sensing elements 302 to measure bladder characteristics from multiple locations in the bladder simultaneously.

Although FIG. 6A illustrates six longitudinal legs 602 and four circumferential legs 604, end-effector assembly 106 may include any number of members having any desired pattern or configuration. For example the members may be cylindrical, square, semi-circular, rectangular, or any other suitable shape. In addition, the members may be any cross-sectional shape known in the art, but not limited to, circular, square, or ovular. Legs 304 may be constructed from a material such as, for example but not limited to, a shape memory material so that the legs may collapse to have a smaller cross-section in the collapsed state.

Figure 6B:
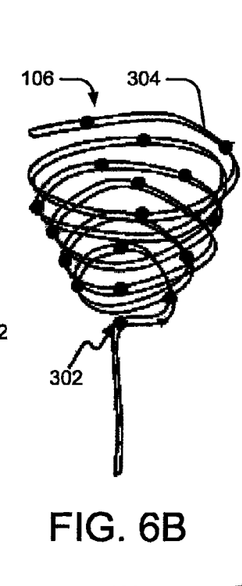
Figures 6C, 6E:
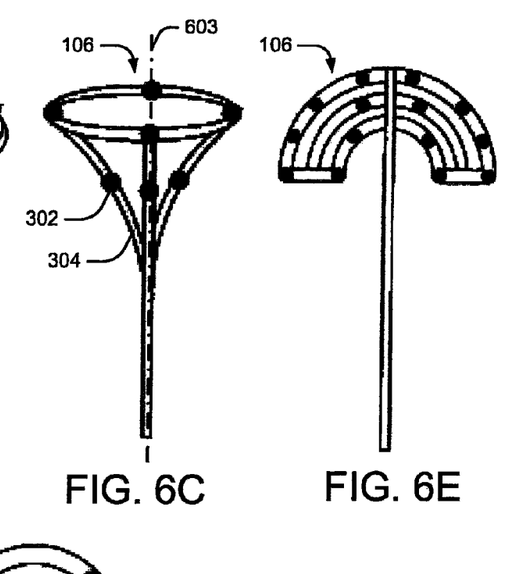

FIG. 6B illustrates an inflatable end-effector assembly 106 having a helical configuration preferably tapering from a larger diameter at distal end 114 to a smaller diameter at the assembly's proximal end 112. One or more sensing elements 302 may be disposed along the exterior surface of the helical structure. It will be understood that alternatively, end-effector assembly 106 may taper from proximal end 112 to a distal end 114. FIG. 6C illustrates an end-effector assembly 106 having multiple legs 602 curving away from a longitudinal axis 603 of end-effector assembly 106. In some embodiments, a circumferential leg 604 (shown in FIG. 6C) may join the distal ends of the legs.

Figure 6D:
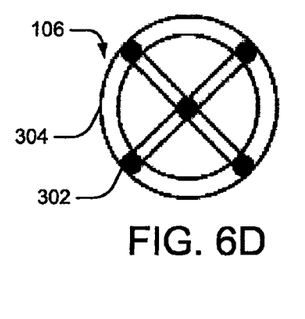

FIGS. 6D and 6E depict end-effector assemblies having a mesh configuration. In particular, end-effector assembly 106 shown in FIG. 6E may have a circular shape; while end-effector assembly 106 shown in FIG. 6D may have a semi-circular shape. Additionally, the end-effector assemblies may be planar, concave, or convex without departing from the scope of the present disclosure. In other embodiments, the end-effector assembly 106 may be an inflatable structure, such as a balloon with sensing elements 302 disposed on an exterior surface of structure.

The end-effector assembly 106 may be formed from the same piece of material as elongate member 102. Alternatively, end-effector assembly 106 may be fabricated independently by suitable known means and may be made integral with or connected to elongate member 102. The connection may be accomplished through any suitable method, such as welding, soldering, or crimping. Elongate member 102 and end-effector assembly 106 may be temporarily connected, allowing operators to fix different end-effector assemblies on top of the same elongate member. Snap fit or screw fit arrangements may be utilized to temporarily connect elongate member 102 and end-effector assembly 106.

Figure 7:
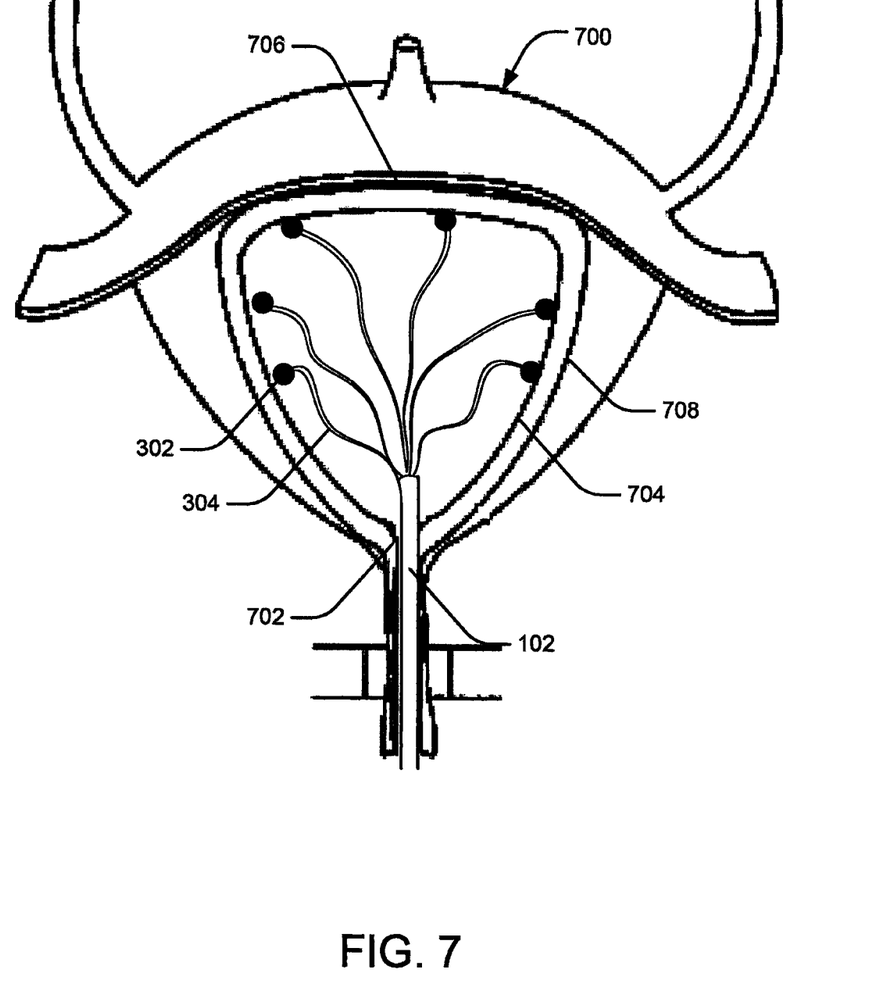
FIG. 7 illustrates the medical device of FIG. 4 being inserted into a vesicle or lumen of a urinary tract of a body, according to embodiments of the present disclosure.

FIG. 7 illustrates an exemplary method for monitoring a urinary tract condition, such as, for example, an overactive bladder (OAB), employing the device of the present disclosure. Medical device 100 may be inserted into the urethra for access to the internal sphincter 702, trigone 704, or dome 706 of the bladder 700. In some embodiments, when medical device 100 is placed against an outer bladder wall 708, surgical access for placement against the outer bladder wall 708 may be achieved using a pelvic floor repair procedure or a laparoscopic procedure. It is to be understood that, in addition to the urinary bladder, medical device 100 may be employed in any visceral organ to detect and monitor abnormal organ function.

In one embodiment, medical device 100 may be advanced to the bladder through sheath 202. Once the sheath's distal end is positioned in the bladder, the operator may place end-effector assembly 106 in the operating (or expanded) state. In the expanded, deployed configuration, end-effector assembly 106 may be configured to conform to the shape of, e.g., a patient's bladder. In addition, when expanded, end-effector assembly 106 may be used to distend portions of the bladder wall, to, e.g., ensure sensing elements 302 are sufficiently positioned against the bladder wall. For example, this state may be accomplished by pulling sheath 202 proximally relative to elongate member 102 or pushing elongate member 102 distally relative to sheath 202. Any suitable handle portion 104 may actuate end-effector assembly 106 as described previously. In the case of steerable legs, the physician may steer legs 304 to the desired location. Once in place, different sensing elements 302 may be activated to measure bladder characteristics. Subsequently, the physician may bring end-effector assembly 106 back in the collapsed state and retrieve medical device 100.

In another embodiment, sensing elements 302 may be implanted in the bladder for long term bladder monitoring. Here, sensing elements 302 may be anchored to the bladder urothelium or detrusor adventitia using sutures, clip anchors, adhesives, or any other such anchoring mechanism. Alternatively, sensing element 302 may be disposed within the bladder in a free-floating configuration. The free-floating sensing elements may be disposable sensing elements that are easily flushed out of the body when a patient urinates.

In some other embodiments, sensing element 302 may be fabricated from biodegradable or bioresorbable material. A biodegradable or bioresorbable material is a material that can decompose or degenerate into a material that has water solubility such that, upon exposure to a body fluid, the material dissolves or erodes over time. In other implementations, the sensing element material may not be soluble, but degenerate into sufficiently fine size particles that can be suspended in the body fluid and transported away from the implantation site without clogging the flow of body fluid. As a result, sensing element 302 is eliminated from the body by excretion in perspiration, urine, or feces; or it can be dissolved, degraded, or metabolized into soluble components that are then excreted from the body once sensing element 302 has completed monitoring the urinary bladder. In addition, the material is biocompatible, which is compatible with living tissue or a living system, non-toxic or non-injurious, and does not cause immunological reaction or rejection. Sensing element 302 may be fabricated using any suitable materials including, for example, but not limited to, metals, non-metal, memory metals such as Nitinol, or polymers.

Figure 8:
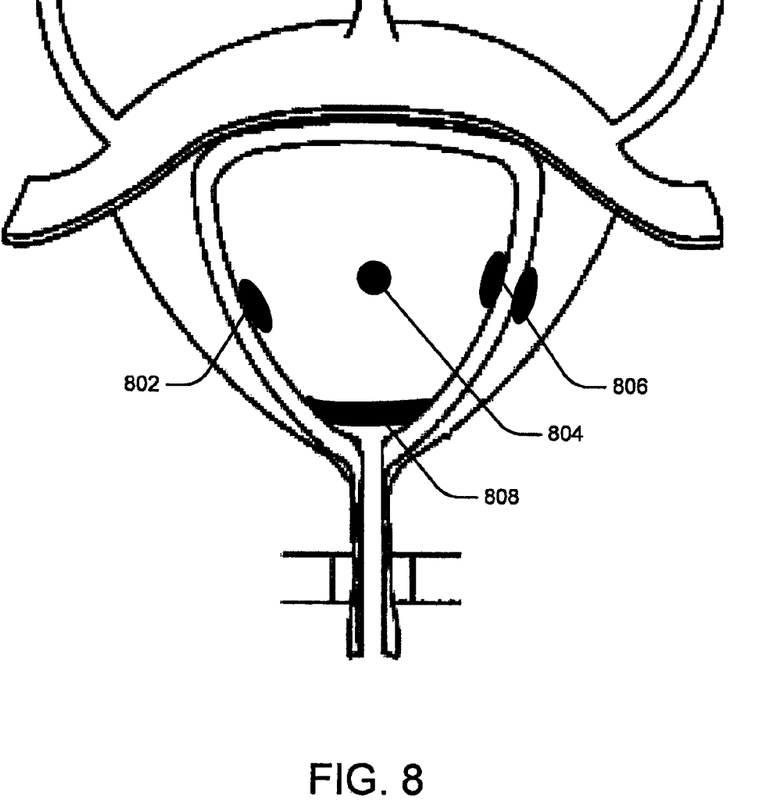
FIG. 8 illustrates exemplary sensing elements and their placement within a portion of the urinary tract of a body, according to embodiments of the present disclosure.

FIG. 8 illustrates exemplary wireless sensing elements 802-808 in the urinary bladder. It will be understood that the shape, size, and position of the sensors depicted in FIG. 8 is merely exemplary to describe the concepts of the present disclosure. For example, although FIG. 8 illustrates four wireless sensing elements 802-808, the disclosed embodiments may include a greater or lesser number of wireless sensing elements 802-808. Further, one or more of wireless sensing elements 802-808 may be positioned in any desirable location within a patient urinary system, including, for example, along the bladder wall or at or near one or more of the dome, urethra, and/or trigone. The exact positioning of any of wireless sensing elements 802-808 may be based on the locations of abnormal areas as detected by the sensing embodiments disclosed herein The actual physical attributes of sensing elements 302 may vary substantially from that depicted here. Moreover, in some monitoring applications one sensing element or one sensing element type may be sufficient to monitor bladder conditions. Alternatively, in other applications, multiple sensing elements or multiple types of sensing elements may be required to monitor the bladder condition.

Sensor 804 is a free-floating wireless sensing element that may be utilized to monitor and measure mechanical changes such as intravesical pressure or the concentration of urea in the urine.

Sensor 802 may be a mechanical, chemical, or biochemical sensing element implanted in the bladder wall preferably near the urothelium or the detrusor. Different securing mechanisms may be employed to implant sensing element 804 in the wall. For example, sensing element 802 may include barbs, hooks, malecot wings, or struts to anchor it to the bladder walls. These securing mechanisms grasp the bladder tissues to anchor sensor element 802 in place. Alternatively, sensing element 804 may be surgically sutured to the bladder wall. Sensing elements 806 are implanted both on the outer and inner bladder walls at substantially the same location. These elements may be utilized to measure the thickness of the bladder wall at different times.

In addition to free-floating and implantable sensors, band-type sensors 808 may also be employed which are substantially wrapped around an internal or external portion of the bladder. These sensing elements may be made of elastic material that remains wrapped around the bladder while exerting minimal forces, if any, on the bladder. The band-type sensing elements 808 may be utilized to measure the extent of bladder wall expansion, bladder wall stretching, internal sphincter pressure, external sphincter pressure, and other such bladder characteristics.

As described previously, sensing elements 302 may measure physical, mechanical, or biochemical changes associated with an overactive bladder. As also alluded to above, sensing elements 302 may be positioned and configured to detect changes in any urinary structure associated with the bladder, including, e.g., the bladder neck and/or surrounding nerves or vasculature. For example, pressure, flow, displacement, vibration, voltage, impedance, or Doppler sensors may be utilized to measure physical changes such as bladder wall thickness, bladder wall morphology or pathology. These sensors are widely known in the art and therefore will not be described in detail here. Moreover, it will be understood by one skilled in the art that any other sensing elements utilized to measure physical properties of the bladder are within the scope of the present disclosure.

To measure chemical changes, sensing elements 302 that measure concentration levels of released substances such as potassium, calcium, sodium, or nitrogen oxide may be employed. Sensors that monitor pH levels can also be utilized. To measure biochemical changes, sensors that monitor the levels of certain hormones and chemicals such as prostaglandin acetylcholine, ATP, tachykinins, cytokines, chemokines, nerve growth factors (NGF), or urea may be used. An example of a biosensor that detects nerve growth factor (NGF) may include a sensor, such as an electrode, coated with anti-NGF, such as horseradish peroxidase-conjugated antibody anti-NGF. In the bladder, binding the NGF to the anti-NGF produces a current. The magnitude of this current is proportional to the NGF concentration in the bladder; therefore, by measuring the current, the NGF can be determined.

Preferably, sensing elements that are placed adjacent to or embedded in the bladder wall measure local changes in properties such as pH level, concentrations of released substances, urothelium or detrusor stretching, nerve firing, and so on. Bladder wall thickness may be measured by using Doppler or RF transmitter-receiver pairs placed on the inside and outside surface of the bladder wall (such as sensing elements 806). Time taken by the receiver to detect the transmitted signal may be utilized to determine the thickness. Similarly, to detect bladder wall morphology or pathology, fluorescent dyes may be injected into the bladder. Then, using an optical sensor connected to a fluorescent microscope (or alternatively, a multiphoton microscope or Raman microscope), physicians can determine the wall morphology and pathology.

Sensing elements 302 may be wired or wireless. Wired sensing elements may be connected to a monitoring unit and a signal processing unit that transforms measured data into a readable output using mathematical algorithms, pattern recognition approaches, neural networks, and other data mining approaches. These elements may be utilized when the sensing element 302 is attached to elongate member 102 and is temporarily inserted in the urinary bladder 700 to measure its characteristics. Wireless sensing elements, on the other hand, may be utilized in implantable or long-term sensing elements. These elements may transmit data to an external unit, which in turn may be connected to a monitoring unit and a signal processing unit. Any known wireless communication protocols, such as WiFi, wireless local area network (WLAN), or Bluetooth® may be utilized for data communication between the external unit and the wireless sensing elements. Further, the wireless sensing elements may be activated or powered down remotely through a separate remote activation device or through the external unit. Alternatively, medical device 100 or the sensing elements may include a memory module for recording measurements. These recorded measurements may be retrieved at a later time. For example, when the patient visits a medical officer or at predetermined intervals of time.

In one embodiment, the disclosed sensing elements may monitor the bladder state and, when required, generate alerts. For example, sensing elements 302 may remind patients to take drugs. To this end, the measurements from sensing elements that monitor the intravesical pressure may be compared with a configurable threshold value. When the measured value exceeds the threshold, an alert may be generated. Similarly, measurements from other sensors may also be utilized to alert patients and remind them to take their drugs whenever measurements (such as frequency and amplitude of electrical transport across the detrusor, changes in nerve transmission, or increase in frequency of electrical signaling, which typically precedes a wet event) exceed threshold values. Moreover, other sensing elements may alert patients to visit their physicians for checkups, or alert patients if emergency treatment is required. Alerts may be generated by the external unit, which receives timely measurement from the sensing element. The external unit may monitor the received signals and whenever the signals exceed a threshold value, an alert may be generated.

In some embodiments, the alerts and the alerting mechanism may be configured by the operator. For example, alerts may be configured as audio, video, or text, depending on the patient's requirements. Preferably, the patient keeps the external unit on her person at all times. For this purpose, the receiver may be designed as a bracelet, anklet, necklace, or any other such accessory which is easy to wear.

In other embodiments, the sensors may alert physicians about critical conditions such as physiological and morphological changes in the urothelium and detrusor during a procedure or in-office therapy. According to the results, physicians can suggest follow-up treatments or visits.

Sensing elements 302 may be insulated metal electrodes, ion-selective electrodes, optical fibers, or optical fiber bundles with tips functionalized with polymers that may be embedded with dye indicators, biomolecules, or nanoparticles. When the bladder fills up, some bladder properties may fluctuate, making it difficult to measure bladder characteristics accurately. To minimize the effects of these changes, the sensing devices may be powered off or shielded during the bladder filling period.

According to one embodiment, urea sensors may be employed in medical device 100. These sensors may periodically measure the urea level with the bladder. If within a short period of time, the sensor detects urea level fluctuations, medical device 100 may determine that the bladder is filling up and it may power off the other sensing elements until the urea level in the bladder stabilizes. Alternatively, sensing elements 302 may be enclosed in casings. When urine flows into the bladder, sensing elements 302 may mechanically close their casings, thereby shielding themselves from the environment to prevent biofouling. Moreover, if concentration of biomarkers is irrelevant, non-implanted sensing elements may ideally be inserted in an empty bladder to minimize environmental effects on sensor response. Sensing elements 302 may also be powered off when they are not required to monitor the bladder. For example, sensing elements 302 may measure bladder characteristics periodically. In between these monitoring periods, sensing elements 302 may be powered-off or closed.

Before introducing medical device 100 at the desired location, sensing elements 302 may be calibrated. For example, biosensors and chemical sensors may be calibrated before implantation to provide a concentration value for measured compounds. Similarly, other sensing elements may also be calibrated. Variation from the calibrated value may indicate certain characteristics of the body organ. Moreover, these calibrated values may also be utilized by the signal processing unit to calculate threshold values for alerts. In other embodiments, if the value of a biomarker is not of importance, the sensing elements may not be calibrated. In these situations, an increase or decrease in the presence of a substance in the organ may provide sufficient information.

Furthermore, the embodiments of the present disclosure may be combined with any suitable therapeutic treatments. Such treatments may include drug delivery, electrical stimulation, ablation (e.g., RF or cryogenic), any suitable surgical procedure, or any other known therapy. In one embodiment, any of the disclosed sensing embodiments may be made integral with a treatment device. For example, any of the disclosed sensing embodiments may be combined with a device configured to deliver electrical stimulation to one or more areas of the urinary system. In addition, the disclosed methods may include sensing one or more areas of a patient's urinary system, including the bladder, and then treating those areas with a separate device. In those embodiments that include wireless sensors, the wireless sensors may be coupled or otherwise in communication with a device for delivering therapy to a patient's urinary system.

The sensor and therapy delivery device may be coupled in any suitable manner known in the art. For example, the sensor and the device may be configured to communicate wirelessly, through a wired connection, or through an external unit.

Embodiments of the present disclosure may be used in any medical or non-medical procedure, including any medical procedure where monitoring of an organ's activity is desired. In addition, at least certain aspects of the aforementioned embodiments may be combined with other aspects of the embodiments, or removed, without departing from the scope of the disclosure.

Other embodiments of the present disclosure will be apparent to those skilled in the art from consideration of the specification and practice of the embodiments disclosed herein. It is intended that the specification and examples be considered as exemplary only, with a true scope and spirit of the invention being indicated by the following claims.

What is claimed is:

1. A medical device, comprising:
   an elongate member having a proximal end and a distal end; and
   an end-effector assembly extending distally from the distal end of the elongate member, the end-effector assembly including a plurality of independently steerable sensing elements for detecting abnormal organ function, wherein the plurality of sensing elements includes one or more of mechanical, chemical, and biological sensors;
   wherein the end-effector assembly further includes a plurality of longitudinally-extending legs and at least one circumferentially-extending leg which form a three-dimensional sphere, wherein each of the plurality of longitudinally-extending legs and the at least one circumferentially-extending leg defines a lumen therein, and at least a portion of at least one of the plurality of independently steerable sensing elements is disposed within the lumen of a respective one of the plurality of longitudinally-extending legs or the at least one circumferentially-extending leg.

2. The medical device of claim 1, wherein the plurality of longitudinally-extending legs extend from a proximal end of the end-effector assembly to a distal end of the end-effector assembly.

3. The medical device of claim 2, wherein the three-dimensional sphere is configured to transition between a compressed delivery configuration and an expanded deployed configuration.

4. The medical device of claim 1, wherein the end-effector assembly includes an inflatable member and the plurality of sensing elements are disposed about an exterior surface of the inflatable member.

5. The medical device of claim 1, wherein the plurality of sensing elements are configured to detect changes in one of a urinary structure and urine within a bladder.

6. The medical device of claim 1, wherein the plurality of sensing elements are configured to wirelessly transmit sensed data to an external component.

7. The medical device of claim 1, wherein the plurality of sensing elements includes at least one of a pressure sensor, a flow sensor, a displacement sensor, a vibration sensor, a voltage sensor, a Doppler sensor, a chemical sensor, or a biosensor.

8. The medical device of claim 1, wherein each of the plurality of longitudinally-extending legs is tubular.

9. A medical device, comprising:
an elongate member having a proximal end and a distal end; and
an end-effector assembly extending distally from the distal end of the elongate member, the end-effector assembly including a plurality of independently steerable sensing elements for detecting abnormal organ function, wherein the end-effector assembly is configured to transition between a collapsed configuration and an expanded configuration;
wherein the end-effector assembly further includes a plurality of longitudinally-extending legs and at least one circumferentially-extending leg which form a three-dimensional sphere, and wherein each of the plurality of longitudinally-extending legs and the at least one circumferentially-extending leg defines a lumen therein, and at least a portion of at least one of the plurality of independently steerable sensing elements is disposed within the lumen of a respective one of the plurality of longitudinally-extending legs or the at least one circumferentially-extending leg.

10. The medical device of claim 9, wherein the plurality of sensing elements includes one or more of mechanical, chemical, and biological sensors.

11. The medical device of claim 9, further including:
a delivery sheath axially movable relative to the elongate member.

12. The medical device of claim 9, wherein at least one sensing element is movable relative to a leg to which it is coupled.

13. The medical device of claim 9, wherein the plurality of sensing elements includes at least one of a pressure sensor, a flow sensor, a displacement sensor, a vibration sensor, a voltage sensor, a Doppler sensor, a chemical sensor, or a biosensor.

14. The medical device of claim 9, wherein the plurality of sensing elements are configured to detect changes in one of a urinary structure and urine within a bladder.

15. The medical device of claim 9, wherein the plurality of sensing elements are configured to wirelessly transmit sensed data to an external component.

16. A medical device, comprising:
an elongate member having a proximal end and a distal end; and
an end-effector assembly extending distally from the distal end of the elongate member, the end-effector assembly including a plurality of sensing elements for detecting abnormal organ function, wherein each of the sensing elements is independently steerable of one another, and wherein the plurality of sensing elements are configured to transmit sensed data to an external component;
wherein the end-effector assembly further includes a plurality of longitudinally-extending legs and at least one circumferentially-extending leg which form a three-dimensional sphere, wherein each of the plurality of longitudinally-extending legs and at least one circumferentially-extending leg defines a lumen therein, and at least a portion of at least one of the plurality of independently steerable sensing elements is disposed within the lumen of a respective one of the plurality of longitudinally-extending legs or the at least one circumferentially extending leg.

17. The medical device of claim 16, wherein the plurality of longitudinally-extending legs extend from a proximal end of the end-effector assembly to a distal end of the end-effector assembly.

18. The medical device of claim 17, wherein the three-dimensional sphere is configured to transition between a compressed delivery configuration and an expanded deployed configuration.

19. The medical device of claim 16, wherein each of the plurality of sensing elements is configured to transmit sensed data wirelessly.

20. The medical device of claim 16, wherein the plurality of sensing elements are configured to detect changes in one of a urinary structure and urine within a bladder.

* * * * *